United States Patent
Piorkowski

(10) Patent No.: US 7,891,607 B2
(45) Date of Patent: Feb. 22, 2011

(54) PRESSURE SENSOR DEVICE

(75) Inventor: Mitchell J. Piorkowski, Mill Creek, WA (US)

(73) Assignee: The Boeing Company, Chicago, IL (US)

(*) Notice: Subject to any disclaimer, the term of this patent is extended or adjusted under 35 U.S.C. 154(b) by 1162 days.

(21) Appl. No.: 11/582,901

(22) Filed: Oct. 18, 2006

(65) Prior Publication Data

US 2008/0092630 A1 Apr. 24, 2008

(51) Int. Cl.
*B64D 11/00* (2006.01)
(52) U.S. Cl. .................... 244/118.5; 73/386
(58) Field of Classification Search .............. 244/118.5; 73/31.04, 179, 386, 707
See application file for complete search history.

(56) References Cited

U.S. PATENT DOCUMENTS

| | | | | |
|---|---|---|---|---|
| 1,634,961 A | * | 7/1927 | Reeves | 73/179 |
| 2,041,151 A | * | 5/1936 | Rogers | 73/178 R |
| 2,632,374 A | * | 3/1953 | Klemperer | 73/179 |
| 2,753,415 A | * | 7/1956 | Andresen, Jr. | 73/386 |
| 3,852,711 A | * | 12/1974 | Greene | 73/387 |
| 4,130,051 A | * | 12/1978 | Brudnicki | 454/73 |
| 4,167,443 A | | 9/1979 | Noyes et al. | |
| 4,266,517 A | | 5/1981 | Sakakibara et al. | |
| 4,339,955 A | | 7/1982 | Iwasaki | |
| 4,522,359 A | * | 6/1985 | Church et al. | 244/129.4 |
| 4,936,142 A | * | 6/1990 | Davidson | 73/179 |
| 5,551,916 A | * | 9/1996 | Morse, Jr. | 454/340 |
| 6,621,021 B2 | | 9/2003 | Pechhold et al. | |
| 6,733,049 B2 | | 5/2004 | Piorkowski et al. | |
| 6,745,982 B2 | * | 6/2004 | Lehmann | 244/118.5 |
| 6,866,227 B2 | * | 3/2005 | Pratt et al. | 244/129.4 |
| 6,902,137 B2 | * | 6/2005 | Brzeski et al. | 244/118.5 |
| 7,032,863 B1 | | 4/2006 | Piorkowski et al. | |
| 2003/0173458 A1 | | 9/2003 | Bandy et al. | |
| 2005/0178907 A1 | | 8/2005 | Piorkowski et al. | |
| 2005/0218266 A1 | | 10/2005 | Bandy et al. | |
| 2009/0165796 A1 | * | 7/2009 | Aubonnet et al. | 128/204.21 |

FOREIGN PATENT DOCUMENTS

GB 872092 7/1961

* cited by examiner

*Primary Examiner*—Galen Barefoot

(57) ABSTRACT

The invention is directed to a pressure sensor device for sensing decompression in a compartment, such as an aircraft cockpit, and causing a compartment door to be free to open substantially simultaneously in response to the decompression. The pressure sensor comprises a first pressure port and a second pressure port where both pressure ports are open to the compartment, and the second pressure port has a greater flow restriction than the first pressure port, When the pressure sensor is actuated by a difference in pressure between the first pressure port and the second pressure port caused by decompression in the compartment, the pressure sensor sends a signal either via direct wired in series or to a controller to enable movement of a compartment door in response to the decompression.

20 Claims, 2 Drawing Sheets

PRESSURE SENSOR DEVICE

BACKGROUND OF THE INVENTION

1) Field of the Invention

The invention relates to a differential pressure sensor, and more particularly relates to a pressure sensor that can detect decompression within a compartment, such as an aircraft cockpit, without having to measure pressures across the bulkhead, that is, a partition that divides the cockpit and another compartment of the aircraft.

2) Description of Related Art

The United States Government, and in particular, the Federal Aviation Administration (FAA), in response to recent terrorist attacks in the United States and elsewhere in the world, has implemented various regulations designed to prevent terrorists from appropriating mobile platforms such as aircraft, buses, and subways. For example, the United States Government now requires aircraft to include secure cockpit doors that are resistant to terrorist intrusion in an effort to prevent terrorists and unauthorized personnel from gaining access to the cockpit and to the controls of the aircraft. Security systems with enhanced safety features for cockpit doors exist to prevent unauthorized entry into an aircraft cockpit or onto a flight deck and to comply with governmental regulations. Known security systems included cockpit door frame reinforcements, bulletproof materials, improved cockpit door latches and two-sided pressure sensor/aneroid systems. However, while known security systems, such as cockpit door and door frame improvements, adequately prevent access to the cockpit and other restricted areas, conventional reinforced door latch mechanisms are not suitable for use with an aircraft due to pressurization of aircraft cabins and cockpits.

Aircraft cockpits and cabins are pressurized due to the altitude at which most commercial aircraft fly, and they are maintained at a certain pressure to provide crew and passengers with a safe and agreeable flight. However, under certain conditions, the cockpit and cabin may lose pressure and experience a depressurization or decompression situation. Forces associated with such depressurization or decompression situations typically occur very rapidly and can cause the cockpit and cabin to change structurally. Aircraft are required to fly with the cockpit door securely locked to prevent intrusion into the cockpit. However, under a cockpit depressurization or decompression situation, the cockpit door must be opened to allow venting of the cabin area and relieve the now higher pressure on the cockpit/cabin bulkhead therein. Due to the size and rate of the forces exerted on the cockpit door and its associated frame/support structure during depressurization or decompression, conventional latches can jam and prevent the cockpit door from being opened. Moreover, many known pressure sensor/aneroid systems are two-sided in construction, that is, they can only detect a pressure loss within the cockpit by measuring pressure across the bulkhead which is the divider between the cockpit and the passenger cabin area. These known two-sided systems can be problematic in that an individual on the passenger side of the bulkhead can initiate a false trip to the system, which allows the cockpit door to be free to open.

Accordingly, there is a need for an improved security cockpit door pressure sensor that can detect decompression within a compartment, such as an aircraft cockpit, without having to measure pressure across the bulkhead, while still allowing a compartment or cockpit door to be adequately locked to prevent intrusion into the compartment or cockpit during flight, and that does not have the problems associated with known security systems.

SUMMARY OF THE INVENTION

The invention satisfies this need for an improved security cockpit door pressure sensor that can detect decompression within a compartment, such as an aircraft cockpit, without having to measure pressure across the bulkhead, as well as provides a unique, nonobvious, and advantageous system. None of the known systems provides all of the numerous advantages of the invention. Unlike known systems, the device of the invention provides the following advantages: provides a pressure sensor that can detect decompression within a compartment, such as an aircraft cockpit or flight deck, without having to measure pressure across a bulkhead; provides a pressure sensor device that has the ability to sense the pressure loss within a specific time frame during decompression in a compartment, such as an aircraft cockpit, to allow the compartment or cockpit door to be free to open for venting of the payloads area, which in turn, prevents a catastrophic failure of the aircraft; provides a pressure sensor device that is small, inexpensive, and has an overall simpler design with less internal components than known systems; provides a pressure sensor device that is not as noise sensitive as known systems; provides a pressure sensor device having unique components made of materials chosen for their strength and electrical and electronic properties; provides for a one-sided pressure sensor that eliminates the ability of allowing an individual on the passenger side of the bulkhead to initiate a false trip, which would allow the cockpit door to be free to open; and, provides a pressure sensor that is self-adjusting for slow pressure changes within the area of operation, such as a cockpit, a passenger area, or any other enclosed space in which the pressure sensor is used.

The invention provides in one aspect for an aneroid pressure sensor for sensing decompression, wherein the pressure sensor comprises a first pressure port and a second pressure port, and further wherein the pressure sensor is actuated by a difference in pressure between the first pressure port and the second pressure port caused by decompression in an aircraft compartment.

The invention provides in another aspect for a pressure sensor device for sensing decompression in a compartment, the pressure sensor device comprising: a first pressure port positioned on a first side of the pressure sensor device, wherein the first pressure port is connected and open directly on one side of the first pressure port, and the first pressure port is connected and open on an opposite side to a diaphragm having a first diameter; a second pressure port positioned on a second side of the pressure sensor device opposite the first side of the sensor device, wherein the second pressure port is connected and open to a reservoir connected to an orifice, which is connected to a capillary tube, where the capillary tube has a second diameter, such that the second diameter of the capillary tube is smaller in size and has a greater flow restriction than the first diameter of the diaphragm; and, wherein the pressure sensor device is actuated by a difference in pressure between the first pressure port and the second pressure port caused by decompression, and further wherein when the pressure sensor device is actuated, the pressure sensor device is direct wired to enable movement of a compartment door in response to the decompression.

The invention provides in another aspect for a pressure sensor device for sensing decompression in a compartment, the pressure sensor device comprising: a first pressure port positioned on a first side of the pressure sensor device, wherein the first pressure port is connected and open on one side of the first pressure port, and the first pressure port is connected and open on an opposite side to a diaphragm having a first diameter; a second pressure port positioned on a second side of the pressure sensor device opposite the first side of the sensor device, wherein the second pressure port is connected and open to a reservoir connected to an orifice which is connected to a capillary tube, where the capillary tube has a second diameter, such that the second diameter of the capillary tube is smaller in size and has a greater flow restriction than the first diameter of the diaphragm; and, wherein the pressure sensor device is actuated by a difference in pressure between the first pressure port and the second pressure port caused by decompression, and further wherein when the pressure sensor device is actuated, the pressure sensor device sends a signal to a controller to enable movement of a compartment door in response to the decompression.

BRIEF DESCRIPTION OF THE DRAWINGS

The foregoing and other advantages and features of the invention, and the manner in which the same are accomplished, will become more readily apparent upon consideration of the following detailed description of the invention taken in conjunction with the accompanying drawings which illustrate preferred and exemplary embodiments, but which are not necessarily drawn to scale, wherein.

DETAILED DESCRIPTION OF THE INVENTION

The invention now will be described more fully hereinafter with reference to the accompanying drawings, in which some, but not all embodiments of the invention are shown. Indeed, this invention may be embodied in several different forms and should not be construed as limited to the embodiments set forth herein. Rather, these embodiments are provided so that this disclosure will be thorough and complete and will fully convey the scope of the invention to those skilled in the art. Like numbers refer to like elements throughout.

Figure 1:
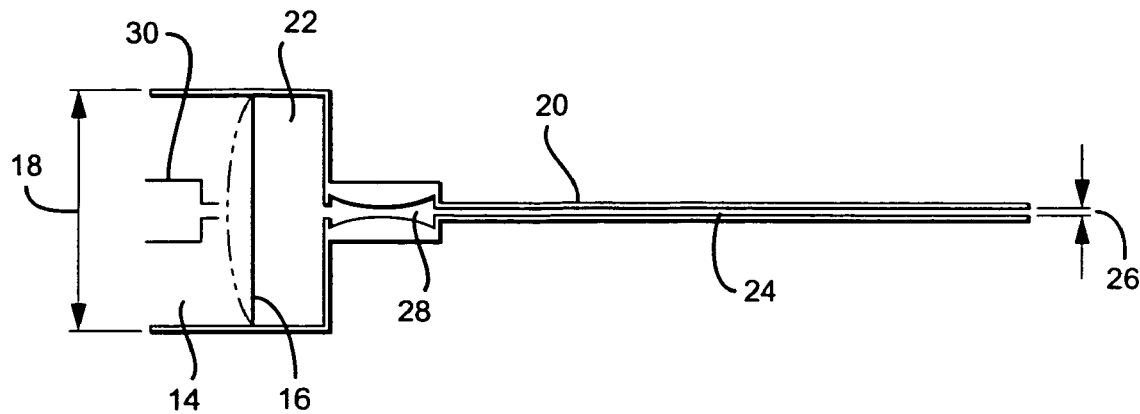
FIG. 1 is a simplified block diagram of the pressure sensor pressure ports of the pressure sensor of the invention.
Figure 2:
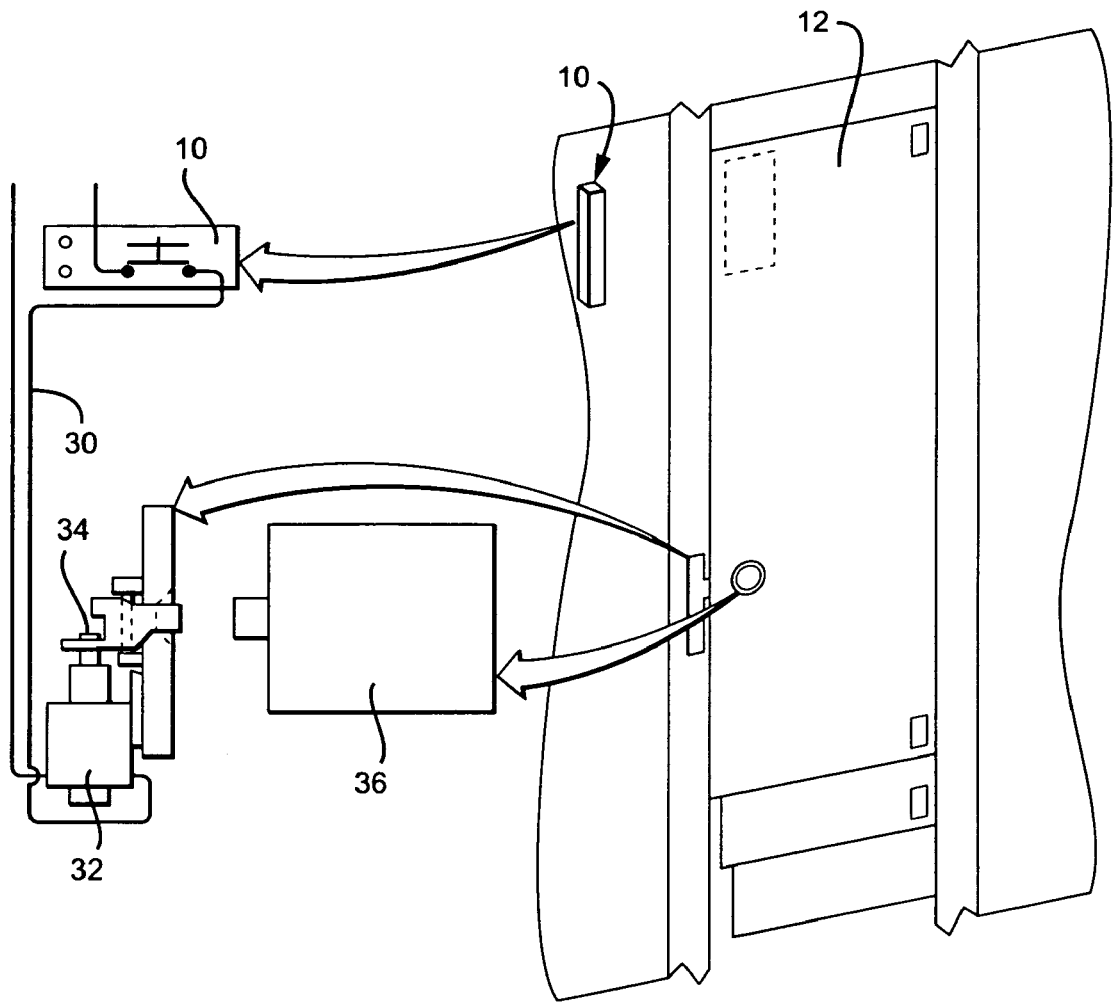
FIG. 2 is a perspective view of an aircraft cockpit door and surrounding area showing the pressure sensor in one embodiment that is direct wired in series; and, FIG. 3 is a perspective view of an aircraft cockpit door and surrounding area showing the pressure sensor in another embodiment where a signal is sent to a logic controller.
Figure 3:
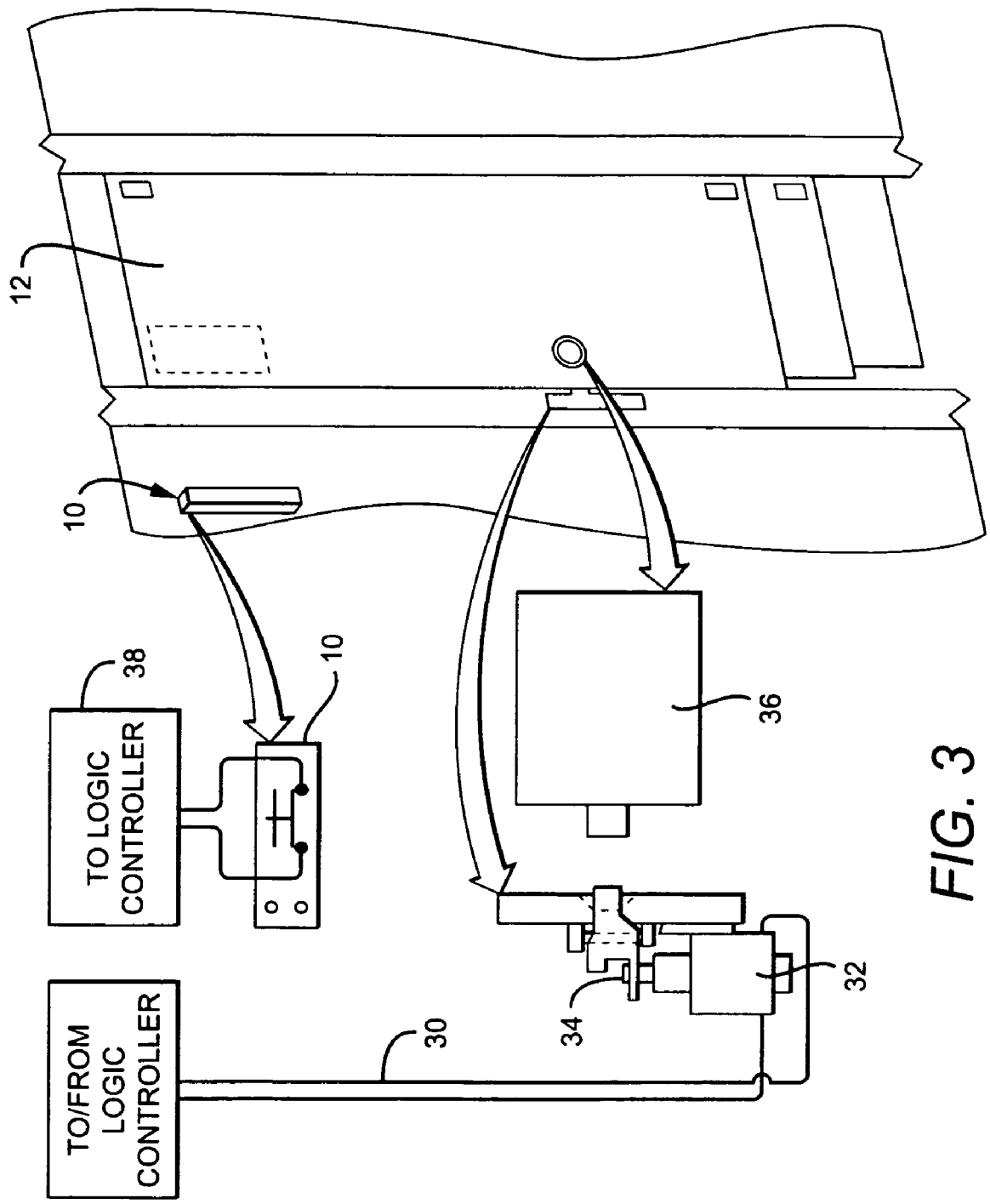

The invention is directed to a differential pressure sensor for sensing decompression, and in particular, rapid decompression, in a compartment, such as an aircraft cockpit, and causing a compartment door to be free to open substantially simultaneously in response to the decompression. Referring now to the drawings, and in particular, to FIG. 1, there is shown a simplified block diagram of the pressure sensor pressure ports of the pressure sensor of the invention. FIG. 2 is a perspective view of an aircraft cockpit door and surrounding area showing the pressure sensor in one embodiment that is direct wired in series. FIG. 3 is a perspective view of an aircraft cockpit door and surrounding area showing the pressure sensor in another embodiment where a signal is sent to a logic controller. As shown in FIG. 2, there is provided a pressure sensor device 10 for use in a compartment, such as an aircraft cockpit, for sensing decompression in the compartment or aircraft cockpit. The pressure sensor 10 enables a compartment door, such as an aircraft cockpit door 12, to be free to open in the event of decompression or depressurization. An example of decompression or depressurization event might be, for example, if the windshield of the aircraft cockpit was broken. Preferably, the pressure sensor is an aneroid. An advantage of the pressure sensor of the invention is that it is one-sided. It can detect decompression or depressurization within the compartment, such as the aircraft cockpit, without having to measure pressure across a bulkhead, that is, an upright partition that divides the cockpit and another compartment of the aircraft, such as a passenger area. As shown in FIG. 1, the pressure sensor device 10 comprises a first pressure port 14 positioned on a first side of the sensor device. The first pressure port 14 is connected and open directly to the compartment or aircraft cockpit via a diaphragm 16 having a first diameter 18. Preferably, the size of the first diameter is about one (1) inch to about one and a half (1½) inches across. Preferably, the diaphragm is constructed of stainless steel, nickel, or other suitable materials that are non-corrosive to the environment that the pressure sensor is operating in. The pressure sensor device 10 further comprises a second pressure port 20 positioned on a second side of the pressure sensor device opposite the first side of the pressure sensor device. The second pressure port 20 is connected and open to the compartment or aircraft cockpit through a reservoir 22 connected at one end to an orifice 28, which is in turn, connected to a lengthy capillary tube 24. The orifice is preferably adjustable. The capillary tube 24 has a second diameter 26. Preferably, the size of the second diameter is about one-eight (⅛) inch across. Preferably, the capillary tube is constructed of stainless steel, nickel, or other suitable materials that are non-corrosive to the environment that the pressure sensor is operating in. Preferably, the length of the capillary tube is from about 2 (two) inches to about 10 (ten) inches long. The second diameter 26 of the capillary tube 24 is smaller in size and has a greater flow restriction than the first diameter 18 of the diaphragm 16. The pressure sensor is designed to sense a depressurization in a single volume or single compartment, and both the first and second pressure ports are open to the same volume or compartment, such as an aircraft cockpit. The first and second pressure ports adjust to changes in the pressure in this compartment or cockpit. The first pressure port has a large area open to the compartment or cockpit and fluid flow into this first pressure port is instantaneous. The second pressure port has the adjustable orifice or opening to allow a delay in equalizing the pressure on either side of the diaphragm of the first pressure port. This delay is based on physical characteristics of the fluid used. Although the preferred fluid used with the invention is air, any compressible fluid may be used. The larger the adjustable opening, the shorter the amount of flow time. The smaller the adjustable opening, the longer the amount of flow time.

The pressure sensor device is actuated by a difference in pressure between the first pressure port and the second pressure port caused by decompression in the compartment or aircraft cockpit. In addition, during normal or non-rapid decompression events, the pressure sensor is self-adjustable in order to equalize pressures on either side of the diaphragm during the non-rapid decompression event. In a first embodiment, as shown in FIG. 2, when the pressure sensor is actuated, the pressure sensor device is direct wired to enable movement of a compartment door in response to the decompression. In one aspect, the pressure sensor device being direct wired in series with a strike solenoid 32 cuts power carried via electrical wires 30 (see both FIG. 2 and FIG. 1) to the strike solenoid 32 which retracts a stop pin 34 that interfaces with a strike arm which in turn interfaces with a latch 36 of the cockpit door, which then allows the cockpit door to be free to open substantially simultaneously in response to decompression. The stop pin 34 interfaces with the strike arm which in turn interfaces with the latch of the cockpit door and stops or prevents the door from being opened. Once the stop pin is moved out of the way, the door is allowed to be free to open. With the direct wired in series embodiment, the pressure sensor senses decompression and breaks the power circuit to the strike solenoid. The power circuit to the strike solenoid is supplied from a power supply located in the system. The strike solenoid has the stop pin attached to it and the stop pin can move up and down. The stop pin is in physical contact with a strike arm which is in contact with the latch of the cockpit door. The pressure sensor opens the electrical circuit to the strike solenoid or other electronic locking mechanism, substantially instantaneously, and this retracts or moves out of the way the stop pin within the electronically operated mechanism, which then can no longer hold the cockpit door in a closed position, thus allowing the cockpit door to be free to open substantially simultaneously in response to the decompression event.

In a second embodiment, as shown in FIG. 3, when the pressure sensor device is actuated, the pressure sensor device sends a signal to a controller 38 to enable movement of a compartment door in response to the decompression. The actuation of the pressure sensor device sends a signal to the controller 38, such as a logic controller component, to cut power via electrical wires 30 to the strike solenoid 32 which retracts the stop pin 34 that interfaces with a strike arm which in turn interfaces with the latch of the cockpit door, which then allows the cockpit door to be free to open substantially simultaneously in response to the decompression event. The pressure sensor is thus used to detect a drop in pressure within the cockpit and to immediately signal this event to the logic controller which would de-energize the strike solenoid. The strike solenoid has the stop pin attached to it and the stop pin can move up and down. The stop pin is in physical contact with a strike arm which is in contact with the latch of the cockpit door. The pressure sensor sends a signal output to the logic controller that in turn would electrically inhibit the strike solenoid or other electronic locking mechanism, substantially instantaneously, from holding the cockpit door in a closed position, thus allowing the cockpit door to be free to open substantially simultaneously in response to the decompression event. Preferably, the logic controller is a computer. However, other suitable logic controllers may be used such as feedback/input devices or analog systems of ladder logic.

With either embodiment, the pressure sensor may be either normally open or normally closed as required by the overall system design. Fluid traveling through the capillary tube and adjustable opening would take a longer period of time than fluid traveling through the first pressure port to the diaphragm. During the time that the fluid travels through the orifice and capillary tube, it would allow activation or movement of the diaphragm in one direction to close or open a circuit. The direction of the motion would be in the direction of the large opening where the pressure drop is instantaneous. The pressure will eventually equalize, but not before the signal to cut the power to the strike solenoid is given and the strike solenoid would drop which would allow the cockpit door to be free to open. Preferably, the cockpit door is allowed to be free to open within 0.005 seconds (5 milliseconds) of the decompression event. The pressure sensor is automatically actuated. The circuitry of/to the pressure sensor may take several forms depending on the overall system design requirements. If the pressure sensor is in an electrical series with the strike solenoid, then this would open the circuit and cut power to the strike solenoid which would allow the door to be free to open. If the pressure sensor is not direct wired in series into the system, then analog ladder logic or system software logic, the close/open, would send a signal to an electrical relay that would cut power to the strike solenoid and allow the door to be free to open. The electrical relay is the controlling element for power to the strike solenoid. In the alternative, this close/open may be a logic sequence for a Programmable Logic Controller (PLC) or other computer to send a signal to an electrical relay or similar device that would cut power to the strike solenoid and would allow the door to be free to open. A decompression, such as a rapid decompression, which is a very violent event, allows the pressure sensor to operate and perform its required function. If there is a pressure change within the compartment or cockpit that is not violent but within non-rapid decompression events or normal operating procedures, then the pressure sensor is self-adjustable to equalize the pressures on either side of the diaphragm so that the diaphragm does not close/open the circuit. Non-rapid decompression events or normal operating procedures may include the aircraft ascending from sea level to 50,000 feet or more, or the aircraft descending or landing at airports that have different elevation levels. With rapid decompression the pressure drop within the cockpit or flight deck has a drop over time (~dp/dt—where "d" means delta or change in, where "p" means pressure, and where "t" means time), depending on the porting of the sensor (see FIG. 1). One side (the first pressure port) drops much faster than the other side (the second pressure port) and this drop over a period of time (before they equalize again) trips the internal contacts (close or open the loop) and this signal, directly or through other electronics (such as a black box), opens the electrical circuit for the strike solenoid, and as such, cuts power to the strike solenoid and drops a stop pin within the strike solenoid that allows the cockpit door to be free to open. The one-sided pressure sensor of the invention eliminates the ability of allowing an individual on the passenger side of the bulkhead to initiate a false trip, which would allow the cockpit door to be free to open. The pressure sensor is small, inexpensive, has an overall simpler design with less internal components, than known sensors, and is not as noise sensitive, which can initiate false trips. The invention includes a switch attached directly to the sensing elements with wiring going out to the strike solenoid, logic controller/computer or into the system so that the system requirements are met. This is all one-sided and within the cockpit or flight deck so false trips or intentional trips from the cabin passenger area by terrorists or unauthorized personnel would be eliminated.

Thus, the invention provides an aneroid pressure sensor for sensing decompression in a compartment, such as an aircraft cockpit, and causing a compartment door or cockpit door to be free to open substantially simultaneously in response to the decompression. The pressure sensor comprises a first pressure port and a second pressure port, where both pressure ports are open to the compartment or cockpit and the second pressure port has a greater flow restriction than the first pressure port. The pressure sensor is actuated by a difference in pressure between the first pressure port and the second pressure port caused by decompression in the compartment such as the aircraft cockpit. The pressure sensor opens the electrical circuit to the strike solenoid or sends a signal to a controller to inhibit power to a strike solenoid to enable the compartment door or cockpit door to be free to open. The invention provides a pressure sensor that can detect a pressure loss within the cockpit or flight deck without having to measure pressure across the bulkhead, that is, an upright partition that divides the cockpit and another compartment of the aircraft, such as a passenger area. The pressure sensor has the ability to sense the pressure loss or decompression within a specific time frame during a cockpit or flight deck decompression event to allow the cockpit or flight deck door to open for venting of the payloads/passenger area, which in turn, prevents a catastrophic failure of the aircraft. The pressure sensor comprises a plurality of unique component made of materials chosen for their strength and electrical and electronic properties. In addition to being useful in an aircraft cockpit, the pressure sensor of the invention may also be used in other closed compartments, such as compartments used in deep sea diving.

Many modifications and other embodiments of the invention will come to mind to one skilled in the art to which this invention pertains having the benefit of the teachings presented in the foregoing descriptions and the associated drawings. Therefore, it is to be understood that the invention is not to be limited to the specific embodiments disclosed that modifications and other embodiments are intended to be included within the scope of the appended claims. Although specific terms are employed herein, they are used in a generic and descriptive sense only and not for purposes of limitation.

What is claimed is:

1. An aneroid pressure sensor for sensing decompression, wherein the pressure sensor comprises a first pressure port and a second pressure port where both pressure ports are connected to and open to a single aircraft compartment, and further wherein the pressure sensor is actuated by a difference in pressure between the first pressure port and the second pressure port caused by decompression in the single aircraft compartment, the pressure sensor being one-sided within the single aircraft compartment to eliminate initiation of a false trip of the pressure sensor outside of the aircraft compartment, and the pressure sensor being able to cause an aircraft compartment door of the single aircraft compartment to be free to open substantially simultaneously in response to the decompression.

2. The pressure sensor of claim 1 wherein the second pressure port has a greater flow restriction than the first pressure port.

3. The pressure sensor of claim 1 wherein the pressure sensor causes the aircraft compartment door to be free to open within 5 milliseconds of the decompression.

4. The pressure sensor of claim 1 wherein when the pressure sensor is actuated, the pressure sensor is direct wired in series to a strike solenoid to enable movement of the aircraft compartment door to be free to open substantially simultaneously in response to the decompression.

5. The pressure sensor of claim 1 wherein the pressure sensor is self-adjusting for pressure changes within the single aircraft compartment.

6. The pressure sensor of claim 1 wherein the first pressure port is connected and open to the single aircraft compartment via a diaphragm having a first diameter.

7. The pressure sensor of claim 1 wherein the second pressure port is connected and open to the single aircraft compartment via a reservoir connected to an orifice, which is connected to a capillary tube, where the capillary tube has a second diameter.

8. The pressure sensor of claim 1 wherein the pressure sensor is normally open.

9. The pressure sensor of claim 1 wherein the pressure sensor is normally closed.

10. The pressure sensor of claim 1, wherein the pressure sensor can detect decompression within the single aircraft compartment without having to measure pressure between the single aircraft compartment and another aircraft compartment.

11. A pressure sensor device for sensing decompression in a single aircraft compartment, the pressure sensor device comprising:
 a first pressure port connected to and open to the single aircraft compartment via a diaphragm having a first diameter, the first pressure port being positioned on a first side of the pressure sensor device;
 a second pressure port connected to and open to the single aircraft compartment via a reservoir connected to an orifice which is connected to a capillary tube, where the capillary tube has a second diameter, the second pressure port being positioned on a second side of the pressure sensor device opposite the first side of the sensor device, wherein the second diameter of the capillary tube is smaller in size and has a greater flow restriction than the first diameter of the diaphragm; and,
 wherein the pressure sensor device is one-sided within the single aircraft compartment to eliminate initiation of a false trip of the pressure sensor device outside of the aircraft compartment, and further wherein the pressure sensor device is actuated by a difference in pressure between the first pressure port and the second pressure port caused by decompression in the single aircraft compartment, and further wherein the pressure sensor device enables movement of an aircraft compartment door of the single aircraft compartment to be free to open substantially simultaneously in response to the decompression.

12. The pressure sensor of claim 11 wherein the aircraft compartment is an aircraft cockpit.

13. The pressure sensor of claim 11 wherein the pressure sensor is self-adjusting for pressure changes within the single aircraft compartment.

14. The pressure sensor of claim 11 wherein the pressure sensor is normally open.

15. The pressure sensor of claim 11 wherein the pressure sensor is normally closed.

16. A pressure sensor device for sensing decompression in an aircraft cockpit, the pressure sensor device comprising:
 a first pressure port connected to and open to the aircraft cockpit via a diaphragm having a first diameter, the first pressure port being positioned on a first side of the pressure sensor device;
 a second pressure port connected to and open to the aircraft cockpit via a reservoir connected to an orifice which is connected to a capillary tube, where the capillary tube has a second diameter, the second pressure port being positioned on a second side of the pressure sensor device opposite the first side of the sensor device, wherein the second diameter of the capillary tube is smaller in size and has a greater flow restriction than the first diameter of the diaphragm; and,
 wherein the pressure sensor device is one-sided within the aircraft cockpit to eliminate initiation of a false trip of the pressure sensor outside of the aircraft cockpit and is actuated by a difference in pressure between the first pressure port and the second pressure port caused by decompression within the aircraft cockpit, and further wherein the pressure sensor device enables movement of an aircraft cockpit door to be free to open substantially simultaneously in response to the decompression, and further wherein the pressure sensor device is self-adjusting for pressure changes within the aircraft cockpit.

17. The pressure sensor of claim 16 wherein the pressure sensor is direct wired in series to a strike solenoid to enable movement of the aircraft cockpit door to be free to open substantially simultaneously in response to the decompression.

18. The pressure sensor of claim 16 wherein the pressure sensor causes the aircraft cockpit door to be free to open within 5 milliseconds of the decompression.

19. The pressure sensor of claim 16 wherein the pressure sensor is normally open.

20. The pressure sensor of claim 16 wherein the pressure sensor is normally closed.

* * * * *